(12) United States Patent
Byers et al.

(10) Patent No.: US 10,126,117 B1
(45) Date of Patent: Nov. 13, 2018

(54) SYSTEM AND METHOD FOR DIFFUSER HOLE INSPECTION

(71) Applicant: General Electric Company, Schenectady, NY (US)

(72) Inventors: Jason Anton Byers, Greenville, SC (US); Anthony Centa, Greenville, SC (US); Zhaoli Hu, Greenville, SC (US); Brian Christopher Wheeler, Greenville, SC (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/595,934

(22) Filed: May 15, 2017

(51) Int. Cl.
| | |
|---|---|
| *G01B 11/00* | (2006.01) |
| *G01B 11/02* | (2006.01) |
| *G01B 11/12* | (2006.01) |
| *G01B 11/24* | (2006.01) |
| *G01N 21/956* | (2006.01) |
| *B23K 26/03* | (2006.01) |

(Continued)

(52) U.S. Cl.
CPC ............ *G01B 11/005* (2013.01); *B23K 26/03* (2013.01); *G01B 11/02* (2013.01); *G01B 11/12* (2013.01); *G01B 11/14* (2013.01); *G01B 11/24* (2013.01); *G01N 21/95692* (2013.01); *F01D 5/005* (2013.01); *G01M 15/14* (2013.01); *G01N 2021/0181* (2013.01)

(58) Field of Classification Search
CPC .... G01M 15/00; G01M 15/02; G01M 15/108; G01M 15/14; G01M 13/00; G01B 11/14; G01B 11/16; G01B 11/24; G01B 11/2408; G01B 11/08; G01B 11/12; G01B 11/02; G01B 11/022; G01B 11/03; G01B 11/002; G01B 11/005; G01B 11/007; G01B 11/28; G01B 11/285; G01B 11/30; G01B 11/303; G01B 11/306; G01N 2021/0118; G01N 2021/0124; G01N 2021/0131; G01N 2021/0137; G01N 2021/0143; G01N 2021/0162; G01N 2021/0181; G01N 2021/8883; G01N 2021/8887; G01N 2021/8918; G01N 2021/9615; G01N 2021/95653; G01N 21/88; G01N 21/8803; G01N 21/9515; G01N 21/954; G01N 21/956; G01N 21/95607; G01N 21/95692; B23K 26/03; B23K 26/032; F01D 5/005; F01D 21/003

See application file for complete search history.

(56) References Cited

U.S. PATENT DOCUMENTS

| | | |
|---|---|---|
| 5,465,780 A | 11/1995 | Muntner et al. |
| 7,574,035 B2 * | 8/2009 | Koonankeil ............ F01D 5/005 |
| | | 348/86 |

(Continued)

*Primary Examiner* — Gordon J Stock, Jr.
(74) *Attorney, Agent, or Firm* — Fletcher Yoder, P.C.

(57) ABSTRACT

A system includes a processor configured to receive a design model for a blade that has multiple diffuser holes. The processor is also configured to generate multiple points along an edge of each of the multiple diffuser holes. Further, the processor is configured to generate multiple vectors and each of the multiple points includes a corresponding vector. Moreover, each of the multiple vectors originates at the corresponding vector's corresponding point. Further, the processor is configured to apply the multiple vectors to inspect one or more manufactured diffuser holes.

20 Claims, 5 Drawing Sheets

(51) Int. Cl.
    *G01B 11/14*     (2006.01)
    *F01D 5/00*     (2006.01)
    *G01M 15/14*     (2006.01)
    *G01N 21/01*     (2006.01)

(56) References Cited

U.S. PATENT DOCUMENTS

| | | | |
|---|---|---|---|
| 8,797,398 B2 * | 8/2014 | Drescher | G01N 21/95692 |
| | | | 348/92 |
| 8,861,673 B2 * | 10/2014 | Michaels | G01B 15/045 |
| | | | 378/4 |
| 9,151,698 B2 * | 10/2015 | Jahnke | G01M 99/002 |
| 9,188,504 B2 * | 11/2015 | Bezdecny | G01M 13/00 |
| 9,310,312 B2 * | 4/2016 | Jahnke | G01N 21/8851 |
| 2006/0229759 A1 | 10/2006 | Luketic et al. | |
| 2014/0257543 A1 * | 9/2014 | Rhodes | G05B 19/4097 |
| | | | 700/97 |
| 2014/0300728 A1 * | 10/2014 | Drescher | G01N 21/95692 |
| | | | 348/92 |
| 2015/0000387 A1 * | 1/2015 | Jiang | F01D 5/147 |
| | | | 73/112.01 |
| 2015/0134301 A1 | 5/2015 | Ramamurthy | |
| 2016/0003607 A1 * | 1/2016 | Reed | G01B 21/20 |
| | | | 73/865.8 |
| 2016/0153865 A1 * | 6/2016 | Lana | G01M 15/14 |
| | | | 73/112.01 |
| 2016/0243655 A1 * | 8/2016 | Hu | B23K 26/032 |
| 2017/0132775 A1 * | 5/2017 | Ramamurthy | G06K 9/4604 |

\* cited by examiner

SYSTEM AND METHOD FOR DIFFUSER HOLE INSPECTION

BACKGROUND

The subject matter disclosed herein relates to a system and method for inspecting, for example, diffuser holes.

Industrial machines, such as gas turbine systems, may provide for the generation of power. For example, the gas turbine systems typically include a compressor for compressing a working fluid, such as air, a combustor for combusting the compressed working fluid with fuel, and a turbine for turning the combusted fluid into a rotative power. For example, the compressed air is injected into a combustor, which heats the fluid causing it to expand, and the expanded fluid is forced through the gas turbine. The gas turbine may then convert the expanded fluid into rotative power, for example, by a series of blade stages of the turbine. The rotative power may then be used to drive a load, which may include an electrical generator producing electrical power and electrically coupled to a power distribution grid. The turbine blades may include diffuser holes to alter the aerodynamics of the blades. The diffuser holes may be used to provide cooling to the turbine blade, to prevent Mach speeds, or other aerodynamic purposes. It may be beneficial to improve the inspection of diffuser holes.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In a first embodiment, a system includes a processor configured to receive a design model for a blade that has multiple diffuser holes. The processor is also configured to generate multiple points along an edge of each of the multiple diffuser holes. Further, the processor is configured to generate multiple vectors and each of the multiple points includes a corresponding vector. Moreover, each of the multiple vectors originates at the corresponding vector's corresponding point. Further, the processor is configured to apply the multiple vectors to inspect one or more manufactured diffuser holes.

In a second embodiment, a method includes receiving, via a processor, a design model for a blade that has multiple diffuser holes. The method also includes generating, via the processor, multiple points along an edge of each of the multiple diffuser holes. Further, the method includes generating, via the processor, multiple vectors and each of the multiple points includes a corresponding vector. Moreover, each of the multiple vectors originates at the corresponding vector's corresponding point. Further, the method includes applying, via the processor, the multiple vectors to inspect one or more manufactured diffuser holes.

In a third embodiment, one or more tangible, non-transitory, machine-readable media including instructions that cause a processor to receive a design model for a blade that has multiple diffuser holes. The instructions also cause the processor to generate multiple points along an edge of each of the multiple diffuser holes. Further, the instructions cause the processor to generate multiple vectors and each of the multiple points includes a corresponding vector. Moreover, each of the multiple vectors originates at the corresponding vector's corresponding point. Further, the instructions cause the processor to apply the multiple vectors to inspect one or more manufactured diffuser holes.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present subject matter will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

Turbine blades within a turbine of a gas turbine engine often include diffuser holes. Diffuser holes are openings that are machined into a turbine blade and are useful for altering the aerodynamics or providing airflow to sections of the turbine blade that would not otherwise receive airflow. For example, the diffuser holes may create surfaces on the interior of the turbine blade. Airflow through the diffuser holes may provide cooling to the created surfaces of the turbine blade. Further, the diffuser holes may alter the aerodynamics of the blade to prevent Mach speeds from occurring or providing improved stability to the turbine blades. Moreover, the diffuser holes may alter the flow of the combustion gases through the turbine. For example, the diffuser holes may mix the combustion gases to provide a more homogenous mixture.

Diffuser holes and the surface of the turbine blade the diffuser holes are machined in may include complex shapes. As such, it may be difficult to perfectly replicate or manufacture a diffuser hole geometry as the geometry is designed in a 3-dimensional (3D) computer aided design (CAD) model. Accordingly, measurements may be taken to determine an accuracy of the manufacturing process. The techniques described herein may allow for a system to automatically determine the accuracy of the manufacturing process using, for example, a photograph of the manufactured diffuser hole.

Figure 1:
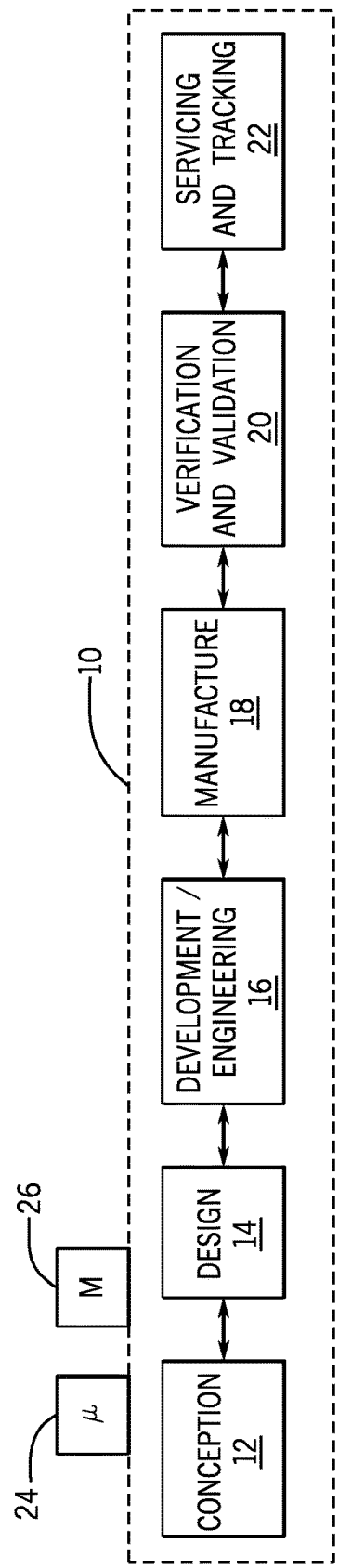
FIG. 1 is a block diagram of an embodiment of a computer-aided technology (CAx) system.

With the foregoing in mind, it may be useful to describe a computer-aided technologies (CAx) system that may incorporate the techniques described herein, for example to improve product lifecycle management (PLM) processes. Accordingly, FIG. 1 illustrates an embodiment of a CAx system 10 suitable for providing for a variety of processes, including PLM processes 12, 14, 16, 18, 20, 22. In the depicted embodiment, the CAx system 10 may include support for execution of conception processes 12. For example, the conception processes 12 may produce a set of specifications such as requirements specifications documenting a set of requirements to be satisfied by a design, a part, a product, or a combination thereof. The conception processes 12 may also produce a concept or prototype for the part or product (e.g., machine). A series of design processes 14 may then use the specifications and/or prototype to produce, for example, one or more 3D design models of the part or product. The 3D design models may include solid/surface modeling, parametric models, wireframe models, vector models, non-uniform rational basis spline (NURBS) models, geometric models, and the like.

Design models may then be further refined and added to via the execution of development/engineering processes 16. The development/engineering processes may, for example, create and apply models such as thermodynamic models, low cycle fatigue (LCF) life prediction models, multibody dynamics (MBD) and kinematics models, computational fluid dynamics (CFD) models, finite element analysis (FEA) models, and/or 3-dimension to 2-dimension FEA mapping models that may be used to predict the behavior of the part or product during its operation. For example, turbine blades may be modeled to predict fluid flows, pressures, clearances, and the like, during operations of a gas turbine engine. The development/engineering processes 16 may additionally result in tolerances, materials specifications (e.g., material type, material hardness), clearance specifications, and the like.

The CAx system 10 may additionally provide for manufacturing processes 18 that may include manufacturing automation support. For example, additive manufacturing models may be derived, such as 3D printing models for material jetting, binder jetting, vat photopolymerization, powder bed fusion, sheet lamination, directed energy deposition, material extrusion, and the like, to create the part or product. Other manufacturing models may be derived, such as computer numeric control (CNC) models with G-code to machine or otherwise remove material to produce the part or product (e.g., via milling, lathing, plasma cutting, wire cutting, and so on). Bill of materials (BOM) creation, requisition orders, purchasing orders, and the like, may also be provided as part of the manufacture processes 18 (or other PLM processes).

The CAx system 10 may additionally provide for verification and/or validation processes 20 that may include automated inspection of the part or product as well as automated comparison of specifications, requirements, and the like. In one example, a coordinate-measuring machine (CMM) process may be used to automate inspection of a manufactured diffuser hole.

A servicing and tracking set of processes 22 may also be provided via the CAx system 10. The servicing and tracking processes 22 may log maintenance activities for the part, part replacements, part life (e.g., in fired hours), and so on. As illustrated, the CAx system 10 may include feedback between the processes 12, 14, 16, 18, 20, 22. For example, data from services and tracking processes 22, for example, may be used to redesign the part or product via the design processes 14. Indeed, data from any one of the processes 12, 14, 16, 18, 20, 22 may be used by any other of the processes 12, 14, 16, 18, 20, 22 to improve the part or product or to create a new part or a new product. In this manner, the CAx system 10 may incorporate data from downstream processes and use the data to improve the part or to create a new part.

The CAx system 10 may additionally include one or more processors 24 and a memory system 26 that may execute software programs to perform the disclosed techniques. Moreover, the processors 24 may include multiple microprocessors, one or more "general-purpose" microprocessors, one or more special-purpose microprocessors, and/or one or more application specific integrated circuits (ASICS), or some combination thereof. For example, the processors 24 may include one or more reduced instruction set (RISC) processors. The memory system 26 may store information such as control software, look up tables, configuration data, etc. The memory system 26 may include a tangible, non-transitory, machine-readable medium, such as a volatile memory (e.g., a random access memory (RAM)) and/or a nonvolatile memory (e.g., a read-only memory (ROM), flash memory, a hard drive, or any other suitable optical, magnetic, or solid-state storage medium, or a combination thereof).

Figure 2:
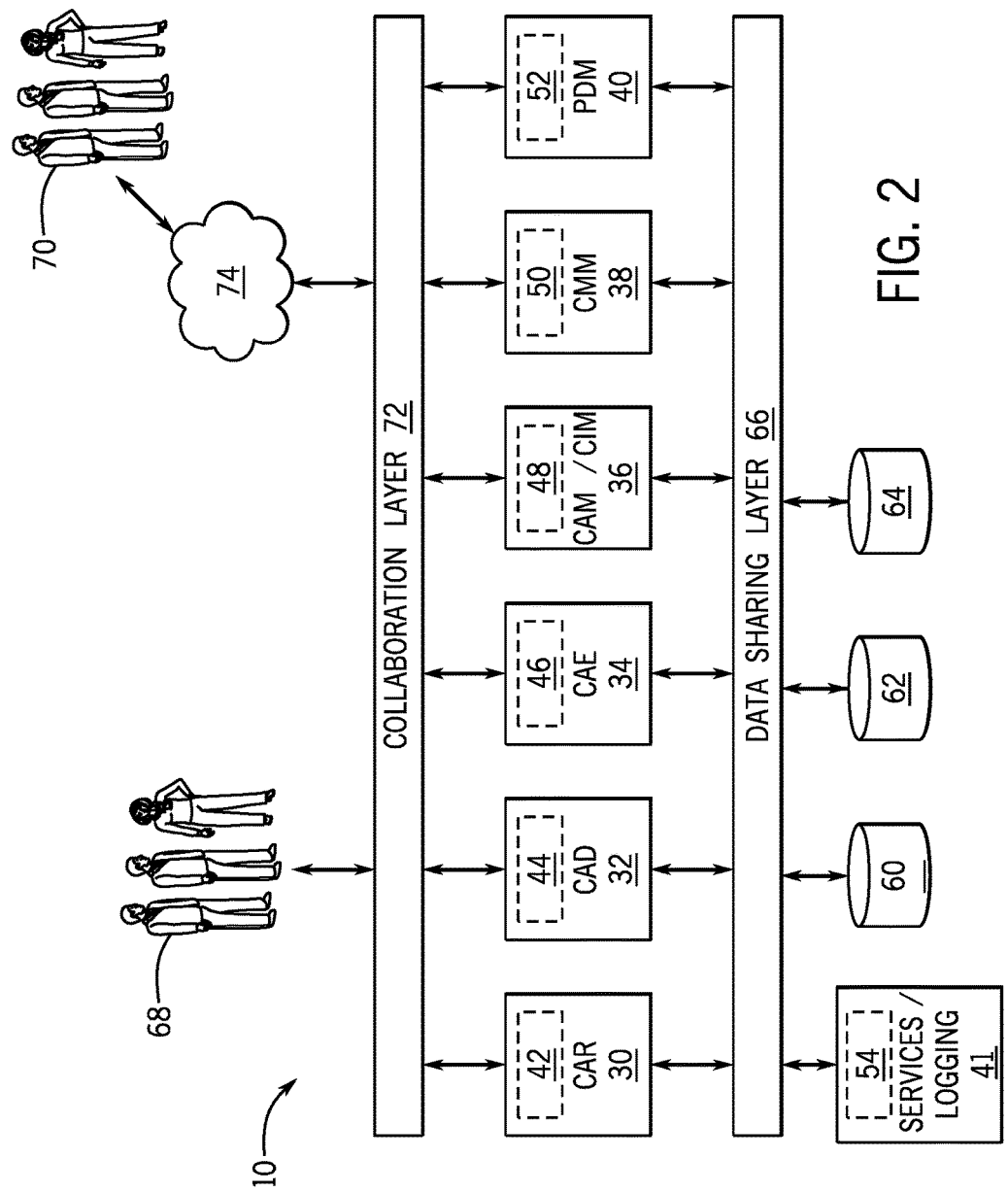
FIG. 2 is a block diagram of a certain components of the CAx system of FIG. 1.

The memory system 26 may store a variety of information, which may be suitable for various purposes. For example, the memory system 26 may store machine-readable and/or processor-executable instructions (e.g., firmware or software) for the processors' 24 execution. In one embodiment, the executable instructions include instructions for a number of PLM systems, for example software systems, as shown in the embodiment of FIG. 2. More specifically, the CAx system 10 embodiment illustrates a computer-aided requirements capture (CAR) system 30, a computer-aided design (CAD) system 32, a computer-aided engineering (CAE) system 34, computer-aided manufacturing/computer-integrated manufacturing (CAM/CIM) system 36, a coordinate-measuring machine (CMM) system 38, and a product data management (PDM) system 40. Each of the systems 30, 32, 34, 36, 38 and 40 may be extensible and/or customizable, accordingly, each system 30 may include an extensibility and customization system 42, 44, 46, 48, 50, and 52, respectively. Additionally, each of the systems 30, 32, 34, 36, 38 and 40 may be stored in a memory system, such as memory system 26, and may be executable via a processor, such as via processors 24.

In the depicted embodiment, the CAR system 30 may provide for entry of requirements and/or specifications, such as dimensions for the part or product, operational conditions that the part or product is expected to encounter (e.g., temperatures, pressures), certifications to be adhered to, quality control requirements, performance requirements, and so on. The CAD system 32 may provide for a graphical user interface suitable to create and manipulate graphical representations of 2D and/or 3D models as described above with respect to the design processes 14. For example, the 3D design models may include solid/surface modeling, parametric models, wireframe models, vector models, non-uniform rational basis spline (NURBS) models, geometric models, and the like. The CAD system 32 may provide for the creation and update of the 2D and/or 3D models and related information (e.g., views, drawings, annotations, notes, and so on). Indeed, the CAD system 32 may combine a graphical representation of the part or product with other, related information.

The CAE system 34 may enable creation of various engineering models, such as the models described above with respect to the development/engineering processes 16. For example, the CAE system 34 may apply engineering principles to create models such as thermodynamic models, low cycle fatigue (LCF) life prediction models, multibody dynamics (MBD) and kinematics models, computational fluid dynamics (CFD) models, finite element analysis (FEA) models, and/or 3-dimension to 2-dimension FEA mapping models. The CAE system 34 may then apply the aforementioned models to analyze certain part or product properties (e.g., physical properties, thermodynamic properties, fluid flow properties, and so on), for example, to better match the requirements and specifications for the part or product.

The CAM/CIM system 36 may provide for certain automation and manufacturing efficiencies, for example, by deriving certain programs or code (e.g., G-code) and then executing the programs or code to manufacture the part or product. The CAM/CIM system 36 may support certain automated manufacturing techniques, such as additive (or subtractive) manufacturing techniques, including material jetting, binder jetting, vat photopolymerization, powder bed fusion, sheet lamination, directed energy deposition, material extrusion, milling, lathing, plasma cutting, wire cutting, or a combination thereof. The CMM system 38 may include machinery to automate inspections. For example, probe-based, camera-based, and/or sensor-based machinery may automatically inspect the part or product to ensure compliance with certain design geometries, tolerances, shapes, and so on. For example, a camera of the CMM system 38 may take pictures of a manufactured part so that the manufactured part may be compared (e.g., the geometry, shape, smoothness of the surface) to the design of the manufactured part.

The PDM system 40 may be responsible for the management and publication of data from the systems 30, 32, 34, 36, and/or 38. For example, the systems 30, 32, 34, 36, and/or 38 may communicate with data repositories 60, 62, 64 via a data sharing layer 62. The PDM system 40 may then manage collaboration between the systems 30, 32, 34, 36, and/or 38 by providing for data translation services, versioning support, archive management, notices of updates, and so on. The PDM system 40 may additionally provide for business support such as interfacing with supplier/vendor systems and/or logistics systems for purchasing, invoicing, order tracking, and so on. The PDM system 40 may also interface with service/logging systems (e.g., service center data management systems) to aid in tracking the maintenance and life cycle of the part or product as it undergoes operations. Teams 64, 66 may collaborate with team members via a collaboration layer 68. The collaboration layer may include web interfaces, messaging systems, file drop/pickup systems, and the like, suitable for sharing information and a variety of data. The collaboration layer 68 may also include cloud-based systems 70 or communicate with the cloud-based systems 70 that may provide for decentralized computing services and file storage. For example, portions (or all) of the systems 30, 32, 34, 36, 38 may be stored in the cloud 70 and/or accessible via the cloud 70.

Once the design is updated, the part may then be manufactured and then inspected, for example via the CMM system 38. In one embodiment, the CAD system may automatically generate CMM code (e.g., dimension suitable for inspecting the manufactured design). For example, the code (e.g., dimensional measuring interface standard [DMIS] code, CALYPSO code) may include a set of points and a vector extending from the each of the set of points on the diffuser hole or product. The set of points along with the vectors may provide information relating to the geometry of the diffuser hole or product. The CMM system 38 may inspect the diffuser hole or product via a probe, a laser, a camera, and so on to compare the manufactured geometry with the designed geometry. The code may additionally include travel paths, a complete measurement plan, allowable variations, for example, in geometry, and so on.

The extensibility and customization systems 42, 44, 46, 48, 50, and 52 may provide for functionality not found natively in the CAR system 30, the CAD system 32, the CAM/CIM system 36, the CMM system 38 and/or the PDM system 40. For example, computer code or instructions may be added to the systems 30, 32, 34, 36, and/or 38 via shared libraries, modules, software subsystems and the like, included in the extensibility and customization systems 42, 44, 46, 48, 50, and/or 52. The extensibility and customization systems 42, 44, 46, 48, 50, and 52 may also use application programming interfaces (APIs) included in their respective systems 30, 32, 34, 36, and 38 to execute certain functions, objects, shared data, software systems, and so on, useful in extending the capabilities of the CAR system 30, the CAD system 32, the CAM/CIM system 36, the CMM system 38 and/or the PDM system 40. By enabling the processes 12, 14, 16, 18, 20, and 22, for example, via the systems 30, 32, 34, 36, and 38 and their respective extensibility and customization systems 42, 44, 46, 48, 50, and 52, the techniques described herein may provide for a more efficient "cradle-to-grave" product lifecycle management.

Figure 3:
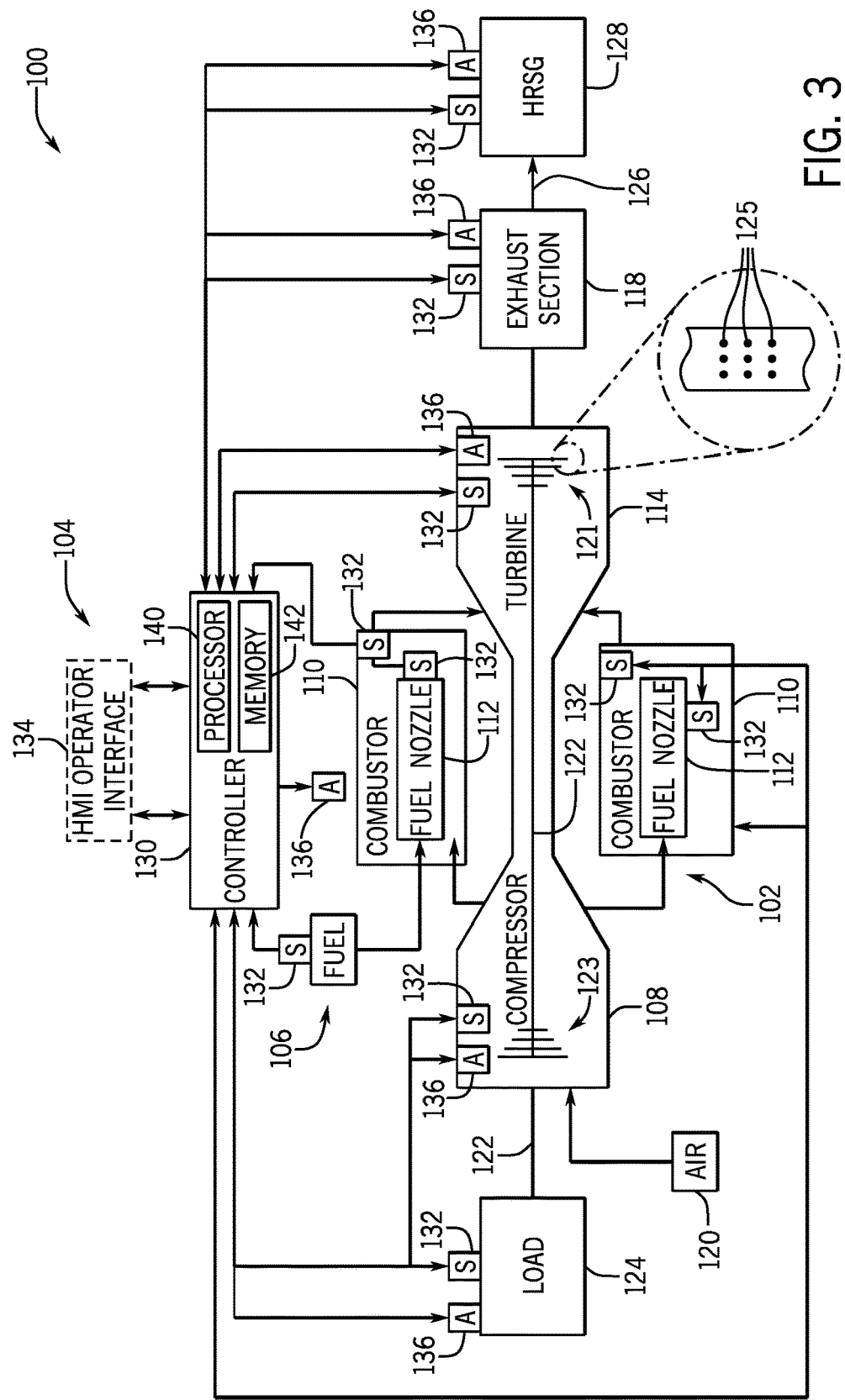
FIG. 3 is block diagram of an industrial system that may be conceived, designed, engineered, manufactured, and/or service and tracked by the CAx system of FIG. 1.

It may be beneficial to describe a machine that would incorporate one or more parts manufactured and tracked by the processes 12, 14, 16, 18, 20, and 22, for example, via the CAx system 10. Accordingly, FIG. 3 illustrates an example of a power production system 100 that may be entirely (or partially) conceived, designed, engineered, manufactured, serviced, and tracked by the CAx system 10. As illustrated in FIG. 1, the power production system 100 includes a gas turbine system 102, a monitoring and control system 104, and a fuel supply system 106. The gas turbine system 102 may include a compressor 108, combustion systems 110, fuel nozzles 112, a gas turbine 114, and an exhaust section 118. During operation, the gas turbine system 102 may pull air 120 into the compressor 108, which may then compress the air 120 and move the air 120 to the combustion system 110 (e.g., which may include a number of combustors). In the combustion system 110, the fuel nozzle 112 (or a number of fuel nozzles 112) may inject fuel that mixes with the compressed air 120 to create, for example, an air-fuel mixture.

The air-fuel mixture may combust in the combustion system 110 to generate hot combustion gases, which flow downstream into the turbine 114 to drive one or more turbine stages. For example, the combustion gases may move through the turbine 114 to drive one or more stages of turbine blades 121, which may in turn drive rotation of a shaft 122. The turbine blades 121 may include a plurality of diffuser holes 125. The diffuser holes 125 may adjust the aerodynamics of the turbine blades 121, as well as provide cooling to the turbine blades 121, to prevent Mach speeds, or for some other aerodynamic purposes.

The shaft 122 may connect to a load 124, such as a generator that uses the torque of the shaft 122 to produce electricity. After passing through the turbine 114, the hot combustion gases may vent as exhaust gases 126 into the environment by way of the exhaust section 118. The exhaust gas 126 may include gases such as carbon dioxide ($CO_2$), carbon monoxide (CO), nitrogen oxides ($NO_x$), and so forth.

The exhaust gas 126 may include thermal energy, and the thermal energy may be recovered by a heat recovery steam generation (HRSG) system 128. In combined cycle systems, such as the power plant 100, hot exhaust 126 may flow from the gas turbine 114 and pass to the HRSG 128, where it may be used to generate high-pressure, high-temperature steam. The steam produced by the HRSG 128 may then be passed through a steam turbine engine for further power generation. In addition, the produced steam may also be supplied to any other processes where steam may be used, such as to a gasifier used to combust the fuel to produce the untreated syngas. The gas turbine engine generation cycle is often referred to as the "topping cycle," whereas the steam turbine engine generation cycle is often referred to as the "bottoming cycle." Combining these two cycles may lead to greater efficiencies in both cycles. In particular, exhaust heat from the topping cycle may be captured and used to generate steam for use in the bottoming cycle.

In certain embodiments, the system 100 may also include a controller 130. The controller 130 may be communicatively coupled to a number of sensors 132, a human machine interface (HMI) operator interface 134, and one or more actuators 136 suitable for controlling components of the system 100. The actuators 136 may include valves, switches, positioners, pumps, and the like, suitable for controlling the various components of the system 100. The controller 130 may receive data from the sensors 132, and may be used to control the compressor 108, the combustors 110, the turbine 114, the exhaust section 118, the load 124, the HRSG 128, and so forth.

In certain embodiments, the HMI operator interface 134 may be executable by one or more computer systems of the system 100. A plant operator may interface with the industrial system 10 via the HMI operator interface 44. Accordingly, the HMI operator interface 134 may include various input and output devices (e.g., mouse, keyboard, monitor, touch screen, or other suitable input and/or output device) such that the plant operator may provide commands (e.g., control and/or operational commands) to the controller 130.

The controller 130 may include a processor(s) 140 (e.g., a microprocessor(s)) that may execute software programs to perform the disclosed techniques. Moreover, the processor 140 may include multiple microprocessors, one or more "general-purpose" microprocessors, one or more special-purpose microprocessors, and/or one or more application specific integrated circuits (ASICS), or some combination thereof. For example, the processor 39 may include one or more reduced instruction set (RISC) processors. The controller 130 may include a memory device 142 that may store information such as control software, look up tables, configuration data, etc. The memory device 142 may include a tangible, non-transitory, machine-readable medium, such as a volatile memory (e.g., a random access memory (RAM)) and/or a nonvolatile memory (e.g., a read-only memory (ROM), flash memory, a hard drive, or any other suitable optical, magnetic, or solid-state storage medium, or a combination thereof).

Figure 4:
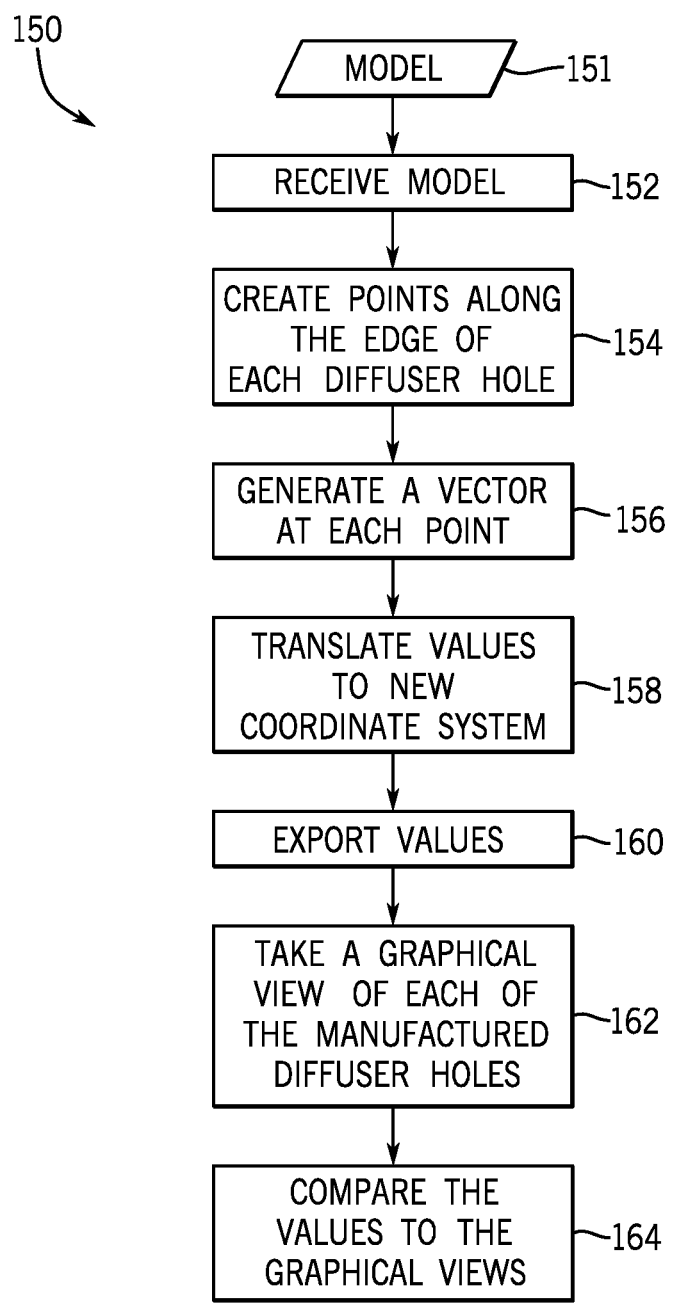
FIG. 4 is a flow chart illustrating an embodiment of a process to aid in the inspection of diffuser holes.

FIG. 4 is a flow chart illustrating an embodiment of a process 150 to aid in the inspection of diffuser holes 125. The process 150 allows an operator to measure the differences between a diffuser hole 125 as it was designed, for example via the CAD system 32, versus a diffuser hole 125 as it was actually manufactured. Although the following process 150 describes a number of operations that may be performed, it should be noted that the process 150 may be performed in a variety of suitable orders. All of the operations of the process 150 may not be performed. Further, all of the operations of the process 150 may be performed by the processors 24.

The process 150 may receive (block 152) a CAD model 151 containing the geometry of the diffuser holes as they were designed in, for example, the CAD system 32. After receiving the CAD model 151, the process 150 may identify the elements in the CAD model 151 that are the diffuser holes 125. This information can be entered manually by a user, or the processors 24 may automatically identify the diffuser holes 125.

Then, the process 150 may create (block 154) points along an edge (e.g., the intersection of the surface of the blade 121 and an interior passage of the diffuser hole) of each diffuser hole contained within the CAD model 151. In the present embodiment, the process 150 creates eighty, evenly spaced points along the edge of the diffuser holes; however, it should be appreciated that the process 150 may create more or less points, including 10, 20, 30, 50, 80, 100, 200 or more. Further, the process 150 may create unevenly spaced points. For example, the process 150 may create more closely spaced points along a curved section, and less closely spaced points along a straight section.

Next, the process 150 may generate (block 156) a 3D vector at each point. The generated vectors include a position denoted by (x,y,z), and the vector is notated by (i,j,k). In the present embodiment, the generated vectors are tangent to the surface of the turbine blade and normal to the edge of the diffuser hole. The (x,y,z) and (i,j,k) data provides information relating to the location of the edges of the diffuser hole, and the orientation (e.g., the direction the edge is facing and the angle of the edge with respect to the surface of the blade 121). However, in alternative embodiments, the generated vectors may be at any suitable orientation or angle with respect to the surface of the turbine blade and the edge of the diffuser hole. The generated vectors are generated using the coordinate system of the CAD model 151. In some instances, an inspection machine, such as the CMM system 38, may use a coordinate system different from one used by the model.

In these instances, the process 150 translate (block 158) the values (e.g., the (x,y,z) and (i,j,k) values) from the coordinate system of the model to the coordinate system of the inspection machine. This allows the inspection machine to conduct an inspection using the same geometry that was created in the model.

After translating the values, the process 150 may export (block 160) the values to a file format (e.g., a text or excel file) readable by the inspection machine (e.g., CMM 38). Different inspection machines may import different file formats, and the processors 24 can be configured to export any suitable file format or to transmit the data via wireless or wired connection to the inspection machine.

The inspection machine may take (block 162) a graphical view (e.g., pictures and/or video) of each of the manufactured diffuser holes 125. Taking the graphical views allows the inspection machine to measure each of the manufactured diffuser holes 125 and assign each of the manufactured diffuser holes 125 a location in the coordinate system of the inspection machine.

In some embodiments, the graphical view may include additional information to relate the manufactured diffuser holes 125 to the coordinate system of the inspection machine. For each of the manufactured diffuser holes 125, the inspection machine may assign a similar number of points along the edge of each of the manufactured diffuser holes 125 that are spaced a similar distance apart from one another as the points created in block 154. Further, in some embodiments, the inspection machine may also create a 3D vector for each point along the edge of each of the manufactured diffuser holes 125 in a similar manner described in block 156. The inspection machine can then import or otherwise receive the file containing the values of the vectors generated by the process 150 in block 156. As discussed above, these values correspond to the model of the diffuser holes.

After the inspection machine has received the file and taken the graphical views, the inspection machine may compare (block 164) the values contained within the file to the values included in the graphical view of the manufactured diffuser holes 125. For example, if the manufactured diffuser hole 125 contains no deviation from the diffuser holes in the model, there may be no differences between the values in the file and the values included in the graphical view. Comparing the two sets of values allows the inspection machine to measure the differences between the diffuser holes contained within the CAD model 151 versus the manufactured diffuser holes 125.

Figure 5:
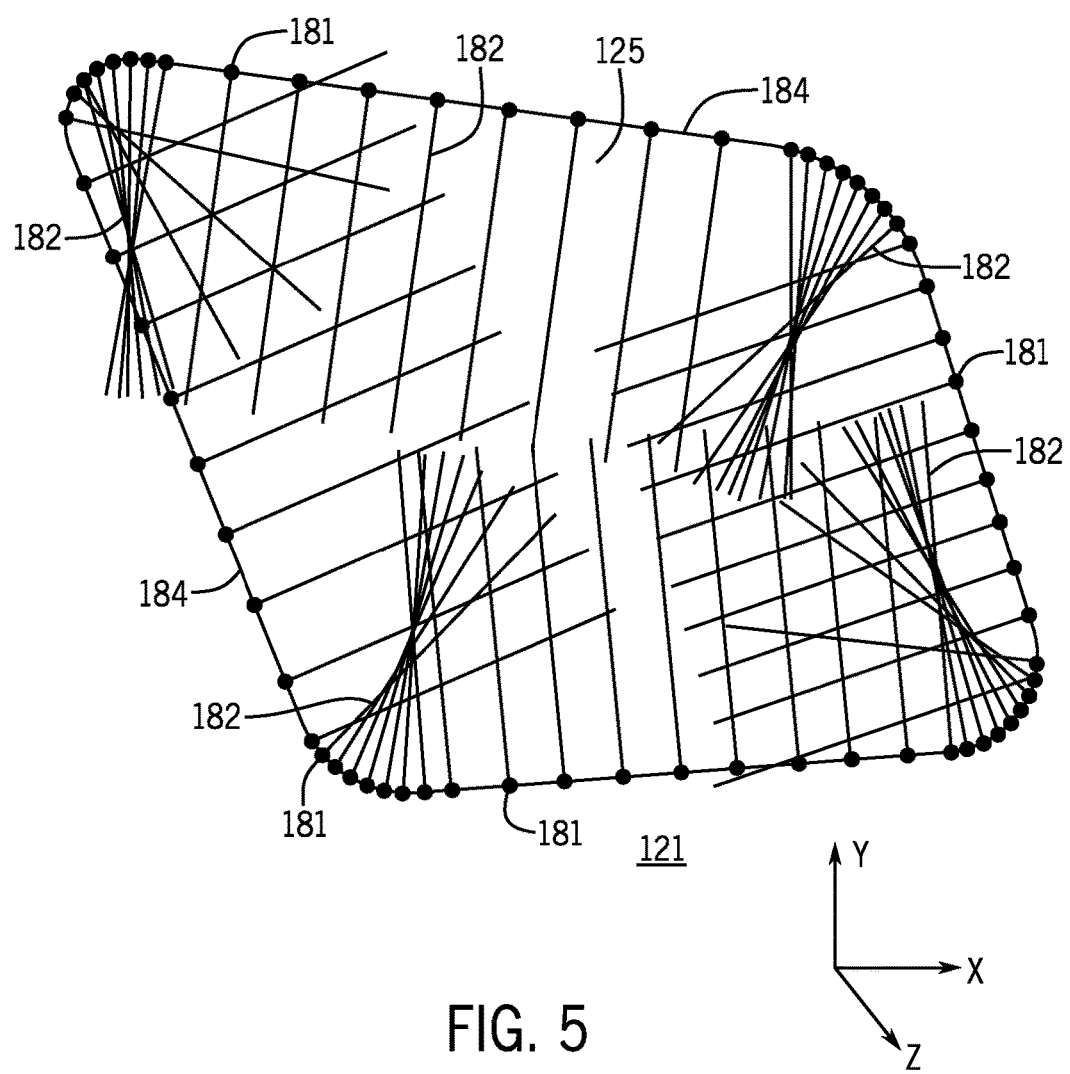
FIG. 5 illustrates an embodiment of a diffuser hole disposed on a surface of a turbine blade with calculated vectors.

FIG. 5 illustrates an embodiment of the diffuser hole 125 disposed on a surface of the turbine blade 121. FIG. 5 also depicts points 181 and calculated vectors 182 extending from the points 181. As discussed above, the points 181 are disposed along an edge 184 that defines the diffuser hole 125. As discussed above, the process 150 may generate vectors 182 that are tangent to the surface of the turbine blade 121 and normal to the edge 184 of the diffuser hole 125. As illustrated, there are approximately eighty calculated vectors 182 extending from approximately eighty points 181, and each are approximately evenly spaced from one another. It should be understood that the even spacing means that the distance along the edge 184 between each adjacent point 181 is approximately the same.

Technical effects include systems and methods for inspecting diffuser holes. A CAD model may contain information relating to the geometry and orientation of a diffuser hole as it is designed. The geometry and orientation of the diffuser hole may be reduced to a number of point and vector coordinates. Once the part is produced, a Coordinate-Measuring Machine (CMM) may inspect a diffuser hole manufactured in accordance with the CAD model. The CMM may take a graphical view that includes a number of measured point and vector coordinates of the manufactured diffuser hole. The CMM may then measure the differences between the point and vector coordinates of the CAD model and the point and vector coordinates of the graphical view. The measured differences may illustrate the differences between the designed diffuser hole and the manufactured diffuser hole. By translating the geometry and orientation of a diffuser hole to a number of point and vector coordinates, the CMM is able to improve the inspection of manufactured diffuser holes more efficiently and accurately.

This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f). This written description uses examples to disclose the subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system comprising:
a processor configured to:
receive a design model for a blade having a plurality of diffuser holes;
generate a plurality of points along an edge of each of the plurality of diffuser holes;
generate a plurality of vectors, wherein each of the plurality of points includes a corresponding vector from the plurality of vectors, and wherein each of the plurality of vectors originates at the corresponding vector's corresponding point; and
apply the plurality of vectors to inspect one or more manufactured diffuser holes.

2. The system of claim 1, wherein each of the plurality of vectors is approximately tangent to a surface of the blade and approximately normal to the edge.

3. The system of claim 1, wherein the plurality of vectors comprises approximately 80 vectors spaced along the edge of each of the plurality of points.

4. The system of claim 1, wherein each of the plurality of vectors is approximately evenly spaced from one another.

5. The system of claim 1, wherein the design model comprises a computer aided design three-dimensional model of the blade.

6. The system of claim 1, wherein the processor is configured to translate each of the plurality of vectors into a first set of values corresponding to a coordinate system of a coordinate measuring machine (CMM) inspection system.

7. The system of claim 6, wherein the CMM inspection system is configured to receive the first set of values and to apply the first set of values to collect one or more pictures, videos, or combination thereof, for each of the one or more manufactured diffuser holes to derive an inspection for the blade.

8. The system of claim 7, wherein the CMM inspection system is configured to derive a second set of values based on the one or more pictures, videos, or combination thereof; wherein the second set of values represents a second plurality of vectors.

9. The system of claim 8, wherein the CMM inspection system is configured to compare the first set of values to the second set of values to derive a suitability of the manufactured inspection holes for use in operations of the blade.

10. A method, comprising:
receiving, via a processor, a design model for a blade having a plurality of diffuser holes;
generating, via the processor, a plurality of points along an edge of each of the plurality of diffuser holes;
generating, via the processor, a plurality of vectors, wherein each of the plurality of points includes a corresponding vector from the plurality of vectors, and wherein each of the plurality of vectors originates at the corresponding vector's corresponding point; and
applying, via the processor, the plurality of vectors to inspect one or more manufactured diffuser holes.

11. The method of claim 10, wherein each of the plurality of vectors is approximately tangent to a surface of the blade and approximately normal to the edge.

12. The method of claim 10, comprising translating, via the processor, each of the plurality of vectors into a first set of values corresponding to a coordinate system of a coordinate measuring machine (CMM) inspection system.

13. The method of claim 12, comprising receiving, via the CMM inspection system, the first set of values and to apply the first set of values to collect one or more pictures, videos, or combination thereof, for each of the one or more manufactured diffuser holes to derive an inspection for the blade.

14. The method of claim 13, comprising deriving, via the CMM inspection system, a second set of values based on the one or more pictures, videos, or combination thereof; wherein the second set of values represents a second plurality of vectors.

15. The method of claim 14, comprising comparing, via the CMM inspection system, the first set of values to the second set of values to derive a suitability of the manufactured inspection holes for use in operations of the blade.

16. One or more tangible, non-transitory, machine-readable media comprising instructions configured to cause a processor to:
receive a design model for a blade having a plurality of diffuser holes;
generate a plurality of points along an edge of each of the plurality of diffuser holes;
generate a plurality of vectors, wherein each of the plurality of points includes a corresponding vector from the plurality of vectors, and wherein each of the plurality of vectors originates at the corresponding vector's corresponding point; and
apply the plurality of vectors to inspect one or more manufactured diffuser holes.

17. The one or more tangible, non-transitory, machine-readable media comprising instructions of claim 16, configured to cause the processor to translate each of the plurality of vectors into a first set of values corresponding to a coordinate system of a coordinate measuring machine (CMM) inspection system.

18. The one or more tangible, non-transitory, machine-readable media comprising instructions of claim 17, configured to cause the CMM inspection system to receive the first set of values and to apply the first set of values to collect one or more pictures, videos, or combination thereof, for each of the one or more manufactured diffuser holes to derive an inspection for the blade.

19. The one or more tangible, non-transitory, machine-readable media comprising instructions of claim 18, configured to cause the CMM inspection system to derive a second set of values based on the one or more pictures, videos, or combination thereof; wherein the second set of values represents a second plurality of vectors.

20. The one or more tangible, non-transitory, machine-readable media comprising instructions of claim 19, configured to cause the CMM inspection system to compare the first set of values to the second set of values.

\* \* \* \* \*